(12) United States Patent
Yamada

(10) Patent No.: US 6,517,347 B2
(45) Date of Patent: Feb. 11, 2003

(54) MOUNTING DISK

(75) Inventor: Tadakatsu Yamada, Saitama (JP)

(73) Assignee: AJS Co., Ltd., Saitama-ken (JP)

( * ) Notice: Subject to any disclaimer, the term of this patent is extended or adjusted under 35 U.S.C. 154(b) by 0 days.

(21) Appl. No.: 09/874,241

(22) Filed: Jun. 6, 2001

(65) Prior Publication Data

US 2001/0051324 A1 Dec. 13, 2001

(30) Foreign Application Priority Data

Jun. 7, 2000 (JP) .................................. 2000-171088

(51) Int. Cl.⁷ .............................................. A61C 11/00
(52) U.S. Cl. ............................................. 433/60; 433/63
(58) Field of Search ............................... 433/60, 61, 62, 433/63

(56) References Cited

U.S. PATENT DOCUMENTS

| | | | | |
|---|---|---|---|---|
| 2,754,588 A | * | 7/1956 | Cordell | 433/60 |
| 4,391,589 A | * | 7/1983 | Monfredo et al. | 433/63 |
| 4,687,442 A | * | 8/1987 | Wong | 433/63 |
| 4,923,398 A | * | 5/1990 | Mackman | 433/60 |
| 5,738,516 A | * | 4/1998 | Landry | 433/60 |
| 5,749,725 A | * | 5/1998 | Chinlund | 433/60 |

OTHER PUBLICATIONS

Patent Abstracts of Japan, Publication No. 2000-042004, Date published Feb. 15, 2000, Inventor: Yamada Tadakatsu.

* cited by examiner

*Primary Examiner*—John J. Wilson
(74) *Attorney, Agent, or Firm*—Browdy and Neimark

(57) ABSTRACT

A mounting disk 60 for a mandible die comprises an upper rotary plate 61 and a lower rotary plate 62. At their extremities, the two plates are rotatably fastened to each other by means of a pivot member 64. If the median points are offset, then the entire mounting disk 60 is turned around a rotational axis provided by a vertical rotary shaft 3 which is fitted to a base of an articulator screwed into a threaded hole 74, to thereby achieve a median registration. If molars are positionally offset in spite of the coincident medial points, then a locking rode 81 is loosened so that the upper rotary plate 61 can turn around a rotational axis defined by the pivot member 64 till the molars come into registration, after which the plates are firmly fixed by the locking rod 81. The angle of rotation at that time is read by use of a scale 76 formed on an arcuate surface 67. More precise fundamental data can thus be obtained for the jaw joint positional coordination.

1 Claim, 11 Drawing Sheets

MOUNTING DISK

FIELD OF THE INVENTION

The present invention relates to a mounting disk adapted to be fitted to a dental articulator for orthodontia and prostheses. The mounting disk is fitted with maxilla and mandible die models to reproduce the relationship of articulation between the upper and lower teeth. More particularly, the invention relates to a mounting disk for a mandible die model.

BACKGROUND OF THE INVENTION

A conventional articulator, e.g., as described in Japanese Patent Laid-Open Publication No. 2000-42004 comprises, as seen in FIGS. 1–3, a pair of posts 2 vertically extending from a base 1, and a rotary plate 3 having one end pivoted to the upper ends of the pair of posts 2 by way of a pair of coordination mechanisms 50. The bottom surface of the rotary plate 3 is provided with a maxilla die mounting disk 5 for providing a maxilla die model 9 thereon. The top surface of the base 1 is provided with a mandible die mounting disk 6 for mounting a mandible die model thereon.

The vertical space between the maxilla die mounting disk 5 and the mandible die mounting disk 6 can be regulated by slide mechanisms 20 provided on the right and left posts 2. The mandible die mounting disk 6 is fitted to the base 1 in such a manner as to allow a displacement in the front-to-rear direction and a displacement in the rotational direction.

More specifically, as seen in FIGS. 13, 14 and 15, the mandible die mounting disk 6 is arranged rotatably relative to the base 1. A vertical rotary shaft 15 is threaded into a threaded hole 13 centrally formed in the mandible die mounting disk 6, the vertical rotary shaft 15 being inserted through a through hole 19 formed in a slider 18 from the opposite side of the base 1. The angle of rotation of the mandible dismounting disk 6 relative to the base 1 can be read using an indicator 36 formed in a seat plate 42 and a scale 37 formed on the circumference of the mounting disk 6.

The setting of the angle of rotation enables that position to be fixed by deeply screwing a guide screw 16 threaded into a threaded hole 26 of the slider 18 into an arcuate guide groove 12 formed in the rear side of the mounting disk 6. Reference numeral 11 denotes a reference groove.

The slider 18 is loosely slidably received in an elongated guide through hole 14 formed in the base 1 so that the slider 18 can be moved in the front-to-rear direction by holding a knob 24 of an operation rod fitted to the slider 18. The movement of the slider 18 allows the mandible die mounting disk to be positionally displaced and regulated in the front-to-rear direction. The distance of displacement can be read by use of a scale 39 formed on the side surface of the base 1 and an indicator 38.formed on the circumference of the mounting disk 6. By setting the distance of displacement, fixation at that position is achieved by means of a fixing screw 25.

The positional offset between the maxilla and mandible die models on the dental articulator can readily be judged by observing the positional offset between the right and left medial cut teeth, i.e., medial points of the maxilla and mandible die models. If the upper and lower medial cut teeth are positionally offset in the right-to-left direction, then the mandible die mounting disk 6 may rotationally be displaced up to a position in which the upper and lower medial cut teeth coincide with each other.

That is, if the upper and lower medial points Q1 and Q2 are positionally offset in the right-to-left direction as seen in FIG. 11a, then the mounting disk 6 may be turned in the direction of R1 around a center p1 of the mandible die mounting disk 6 up to a position in which the upper and lower medial points come into registration.

However, some patients may suffer a positional offset between the upper and lower molars despite registration of the medial points Q1 and Q2 as seen in FIG. 12a. n such an event, attempts to register the molar by rotating in the R1 direction around a mounting disk center p1 may cause a positional offset between the upper and lower medial points Q1 and Q2, as shown in FIG. 12b.

SUMMARY OF THE INVENTION

It is therefore the object of the present invention to overcome the drawbacks of conventional articulators and to provide a mounting disk for a dental articulator having a coordination function to modify the patient's jaw joint position reproduced on the articulator to a proper position in any case.

To achieve the above object, in the present invention, the mandible die mounting disk is vertically segmented into two parts so as to provide a function wherein the mandible die mounting disk is turned around its center axis relative to the articulator base, as well as a function whereby the mandible die mounting disk is turned around the extremity of the mandible die mounting disk, i.e., around the median point thereof.

According to one aspect of the present invention, there is provided a mounting disk comprising a lower rotary plate having at its substantially central portion a mounting portion for a vertical rotary shaft for mounting to a base of an articulator, and an upper rotary plate superposed on top of the lower rotary plate. The upper rotary plate has on its top surface a mandible model fixing portion for mounting a mandible model thereon. The lower rotary plate and the upper rotary plate are rotatably coupled to each other by way of a pivot member disposed at one end of each of the lower and upper rotary plates.

The mounting disk of the present invention may further comprise indication means which indicates a relative position between the lower rotary plate and the upper rotary plate, and locking means arranged to lock a relative position between the lower rotary plate and the upper rotary plate.

Preferably, the indication means includes an indication scale and an indicator. The indication scale indicates a relative position between the lower rotary plate and the upper rotary plate. Both the lower rotary plate and the upper rotary plate have an arcuate surface on their respective side faces opposite the pivot member. The arcuate surface has a center axis coincident with a pivotal axis of the pivot member. The indication scale is provided on the arcuate surface of one of either the lower rotary plate or the upper rotary plate. The indicator is provided on the arcuate surface of the other of the lower rotary plate and the upper rotary plate.

Preferably, the locking means includes an arcuate skirt, a horizontally extending slit formed in the skirt, and a locking rod passing through the slit. The arcuate skirt is formed by extending the arcuate surface of the other of the lower rotary plate and the upper rotary plate so as to cover the indication scale provided on the arcuate surface of the one of the lower rotary plate and the upper rotary plate. The locking rod has an extremity screwed into a threaded hole formed in the arcuate surface having the indication scale. The locking rod has at its midpoint an enlarged portion to fixedly tighten the skirt.

BRIEF DESCRIPTION OF THE DRAWINGS

The above and other objects, aspects, features, and advantages of the present invention will become more apparent from the following detailed description when taken in conjunction with the accompanying drawings, in which.

DETAILED DESCRIPTION OF THE INVENTION

Figure 1:
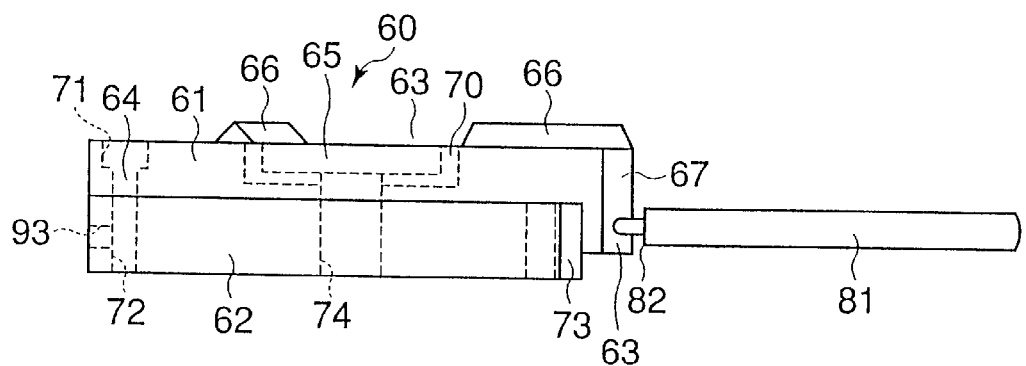
FIG. 1 is a front elevational view of a mounting disk in accordance with the present invention.
Figure 2:
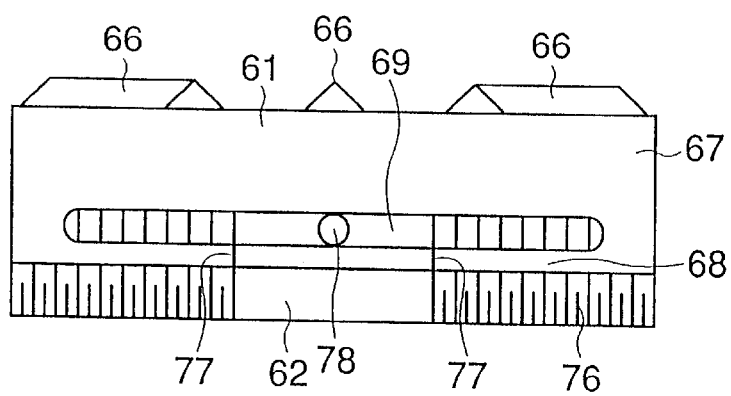
FIG. 2 is a side elevational view of the mounting disk depicted in FIG. 1.
Figure 3:
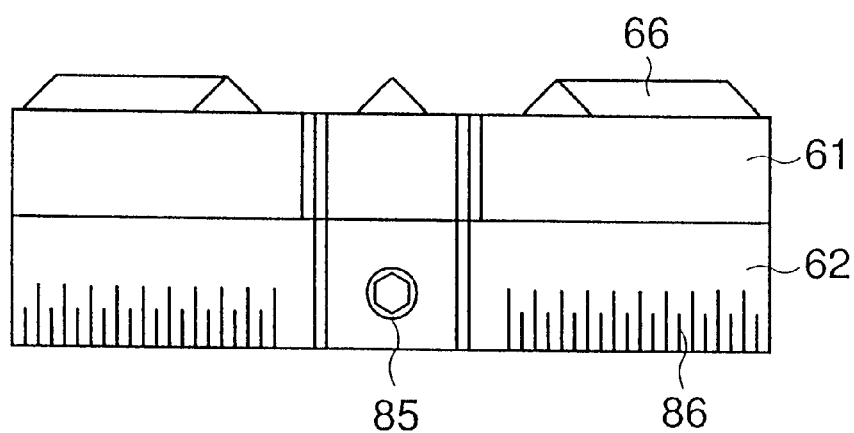
FIG. 3 is another side elevational view of the mounting disk depicted in FIG. 1.
Figure 4:
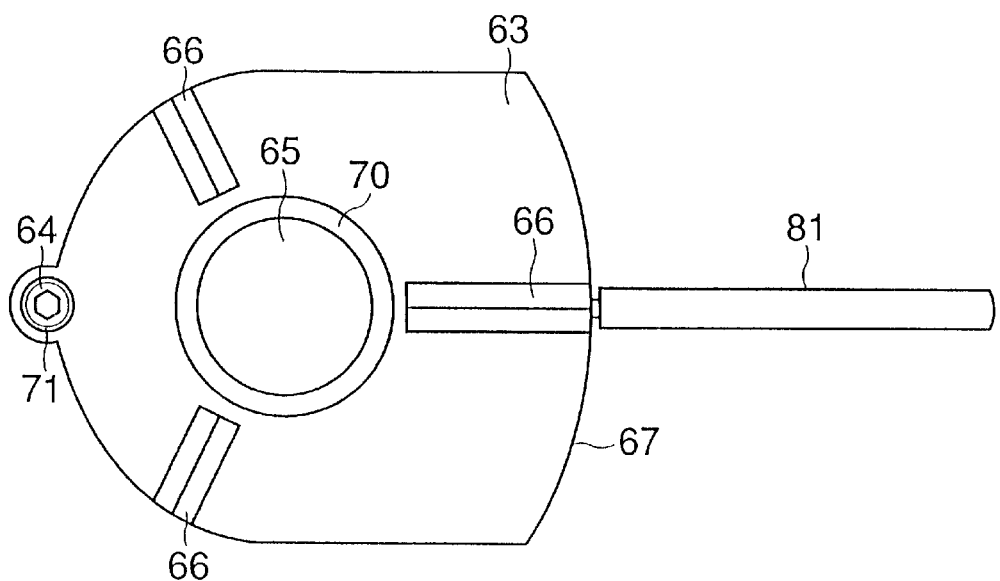
FIG. 4 is a top plan view of the mounting disk depicted in FIG. 1.

Referring to FIGS. 1 to 5, there is depicted a presently preferred embodiment of a mounting disk for a dental articulator in accordance with the present invention. A mounting disk for a mandible die is ge4nerally designated at 60 and comprises an upper rotary plate 61 and a lower rotary plate 62. The upper 61 and lower 62 rotary plates are rotatable at their extremities, i.e., at one end of each of the upper and lower plate relative to each other by means of a pivot member 64. The pivot member 64 is disposed at one end of each of the upper and lower rotary plates, and a vertical line passes through a median point of an incisor of the mandible die to be mounted on the mounting disk.

Figure 7:
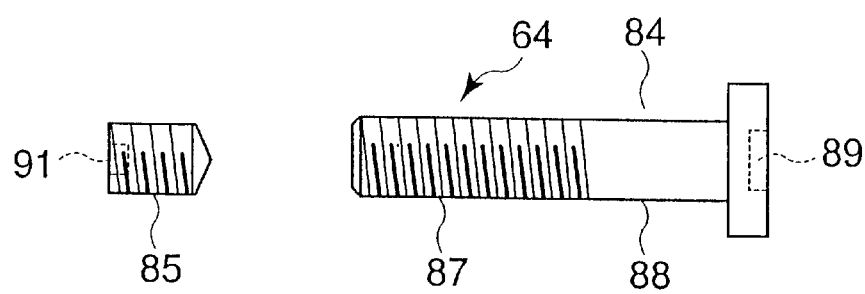
FIG. 7 is an exploded view of a pivot member.

The pivot member 64 includes a bolt 84 and a setscrew 85 as shown in FIG. 7. The bolt 84 has a threaded potion 87 at its lower half and an unthreaded rotary shank 88 at its upper half. The bolt 84 is inserted into a bearing hole 71 formed in the upper rotary plate 61 so that the threaded portion 86 is screwed into a bearing hole 72 formed in the lower rotary plate 62, after which the setscrew 85 is firmly fastened such that the upper rotary plate 61 can rotate around the blot 84 relative to the lower rotary plate 62. Reference number 89 denotes a hexagonal recess formed in the head of the bolt 84 for receiving a screwdriver. Reference number 91 denotes a hexagonal recess formed in the bottom of the setscrew 85 for receiving a screwdriver for the setscrew 85.

The top surface of the upper rotary plate 61 is formed with a mandible model fixing portion 63 for mounting a mandible die model thereon. The mandible model fixing portion 63 is provided with an iron dish 70 and three positioning protuberances 66. The dish 70 receives a permanent magnet 65 to firmly attract by its magnetic force an iron substrate disposed on the bottom surface of the mandible die model so that fixing is achieved by the action of the magnetic force of the permanent magnet 65 itself.

Figure 6:
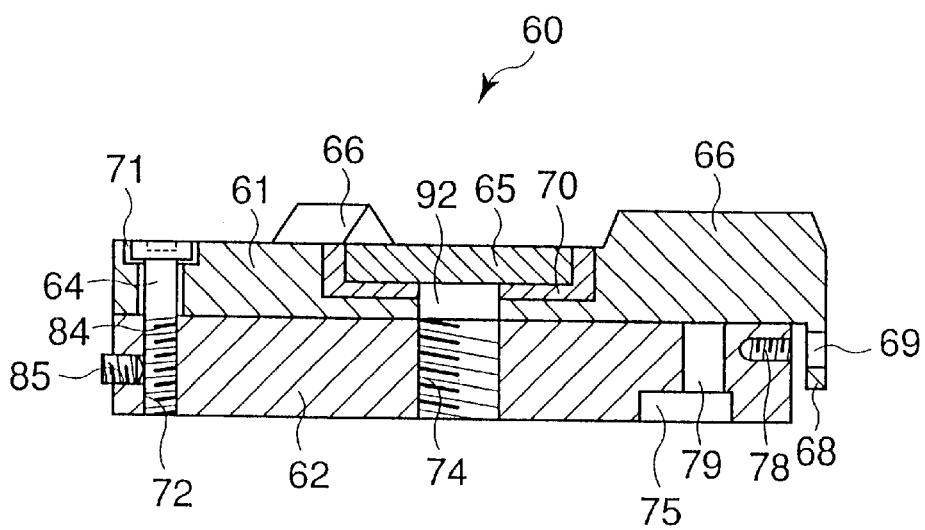
FIG. 6 is a longitudinal sectional view of the mounting disk depicted in FIG. 1.

The dish 70 has at its center bottom a circular hole 92 (FIG. 6), with the underlying upper rotary plate 61 also having a through-hole formed at the center thereof. The through-hole is in communication with a threaded hole 74 formed in the lower rotary plate 62 so that the magnet 65 attractively attached to the dish 70 can be removed by inserting a proper rod into the threaded hole 74 from below the lower rotary plate 62 and using the magnet 65 to raise the rod.

On the side surface opposite the bearing hole 71 for receiving the pivot member 64, the upper rotary plate 61 has an arcuate surface 67, the center axis of which coincides with the longitudinal axis of the pivot member 64. The arcuate surface 67 is extended downward to provide an arcuate skirt 68. The arcuate skirt 68 has at its center a horizontally extending slit 69.

On the side surface opposite the bearing hole 72 for receiving the pivot member 64, the lower rotary plate 62 has an arcuate surface 73, the center axis of which is in alignment with the longitudinal axis of the pivot member 64.

Figure 5:
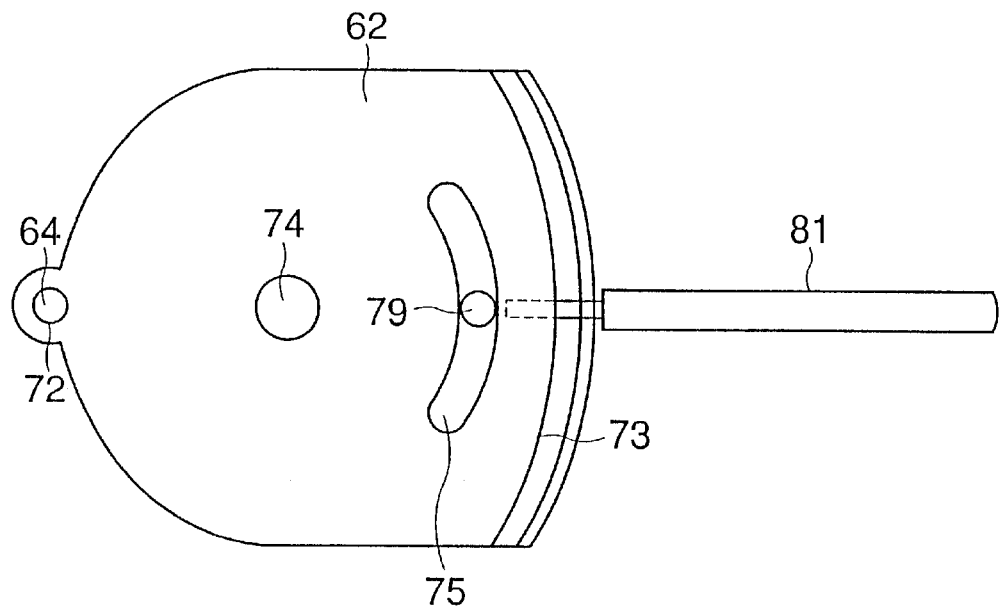
FIG. 5 is a rear plan view of the mounting disk depicted in FIG. 1.

As can be seen from FIG. 5, the lower rotary plate 62 has a through threaded hole 74 substantially at the center of the lower rotary plate. This threaded hole 74 is designed to threadedly engage with a vertical rotary shaft 15 (cf. FIG. 9) of the articulator generally designated at 1. The lower rotary plate 62 has on its bottom surface an arcuate guide groove 75 configured to receive the tip of a guide screw (cf. FIG. 9) of the articulator 1. Reference numeral 79 denotes a reference point hole into which the tip of the guide screw 16 is inserted to allow the mounting disk 60 to be fixedly positioned relative to the base 1.

The arcuate surface 73 is provided with a scale 76 which indicates the relative position between the upper rotary plate 61 and the lower rotary plate 62. The skirt 68 of the upper rotary plate 61 has an indicator 77 for the scale 76.

Figure 8:
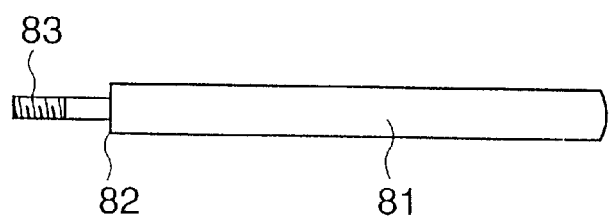
FIG. 8 is a front elevational view of a locking rod.

Reference numeral 81 denotes a locking rod that has at its one end a threaded portion 83 (FIG. 8) to be screwed into a threaded hole 78 formed in the arcuate surface 73 of the lower rotary plate 62. The locking rod 81 has at its midway an enlarged portion 82 whose diameter is enlarged so that when the locking rod 81 is threaded into the threaded hole 78, the enlarged portion 82 is pressed against the skirt 68 of the upper rotary plate 61 so as to allow the upper rotary plate 61 to be firmly secured to the lower rotary plate 62.

A method for using the apparatus of the present invention will now be described.

First, as previously set forth in the description of the related arts, the upper and lower die models are disposed on the upper and lower mounting disks to properly reproduce the current position of the patient's mandibular joint on the articulator.

An X ray of the mandibular joint portion is then taken to observe the condition of the mandibular joint.

Figure 9:
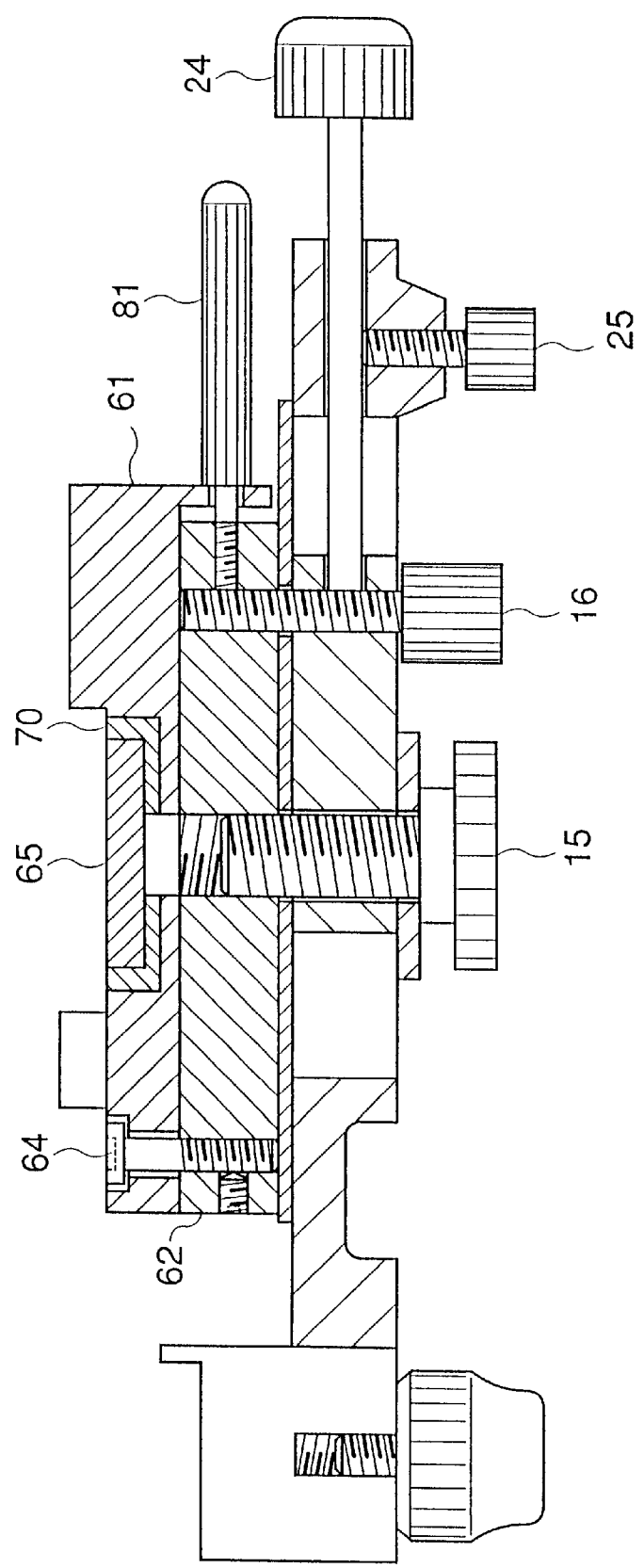
FIG. 9 is a sectional view explaining a method of using the mounting disk of the present invention.

Then, as shown in FIG. 9, the vertical rotary shaft 15 and a fixing craw 25 of the mandible die mounting disk 60 are loosened to achieve a registration in the front-to-back direction between the upper and lower incisors of the die models. The distance of displacement at that time is read from a scale 39, for recording. The vertical position adjustment of the mandible die model is carried out by a slide mechanism 20 of a post 2. The distance of displacement therefor is then measured by a paper-like leaf gauge, for recording.

Figure 11A:
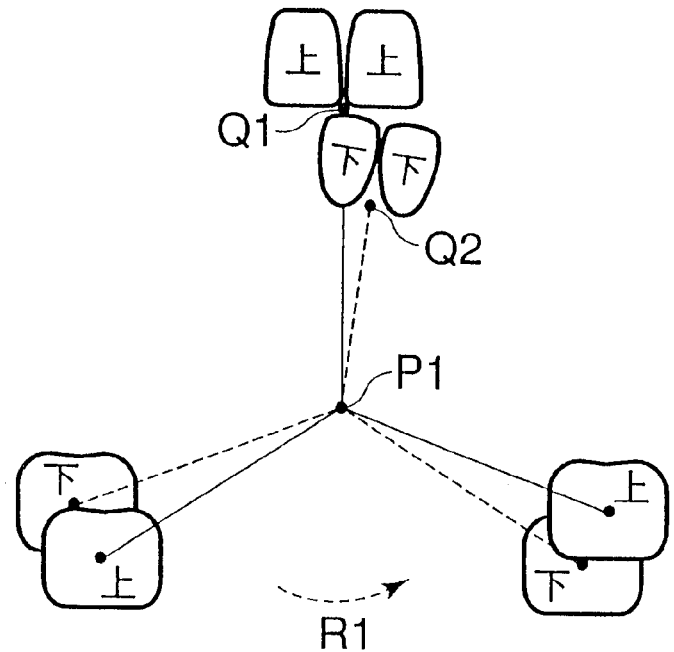
FIG. 11a is an explanatory diagram showing the method of using the mounting disk of the present invention.
Figure 11B:
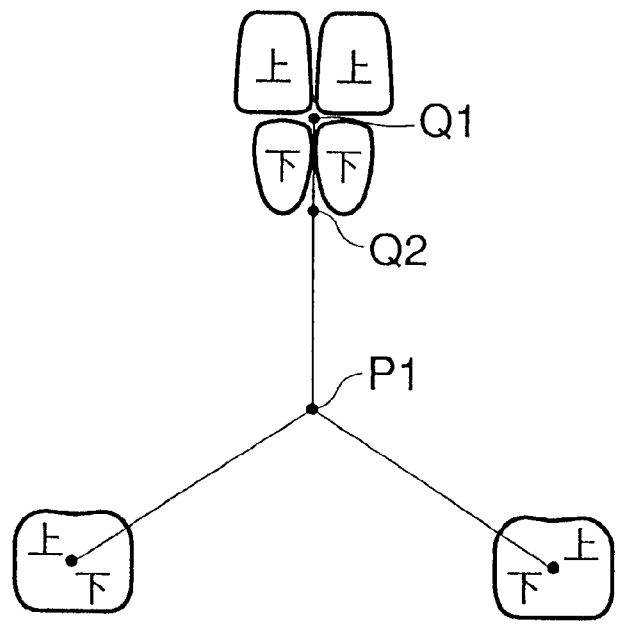
FIG. 11b is an explanatory diagram showing the method of using the mounting disk of the present invention.
Figure 12A:
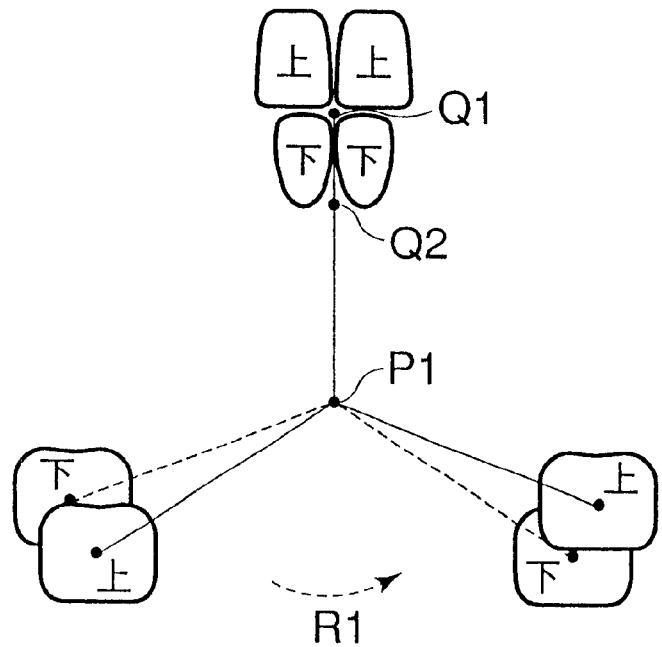
FIG. 12a is an explanatory diagram showing a method of using a conventional mounting disk.
Figure 12B:
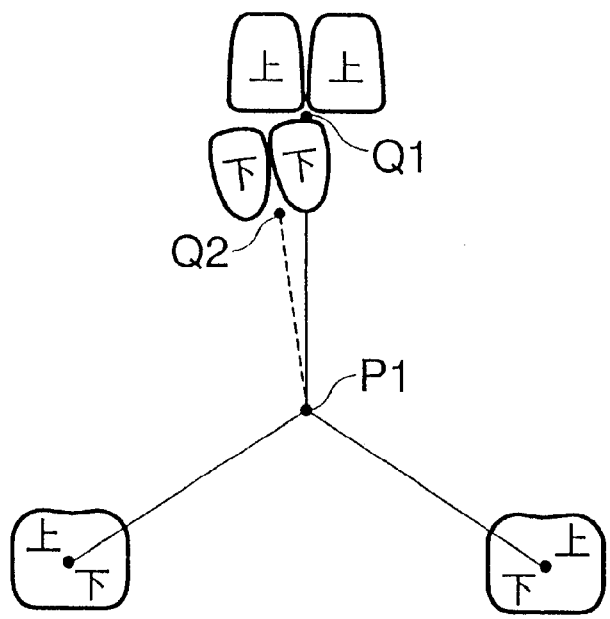
FIG. 12b is an explanatory diagram showing a method of using a conventional mounting disk.
Figure 13:
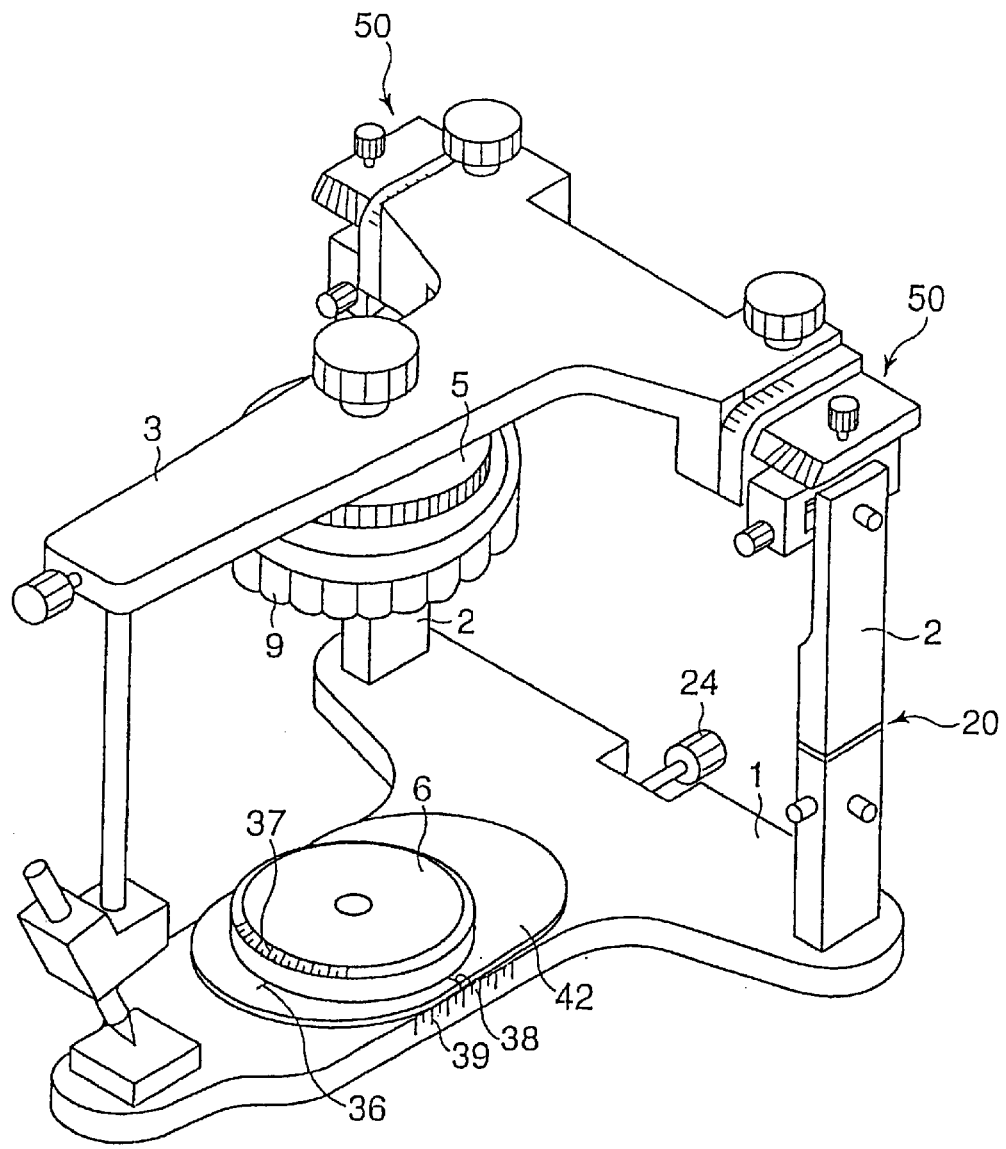
FIG. 13 is a perspective view of a conventional articulator.
Figure 14:
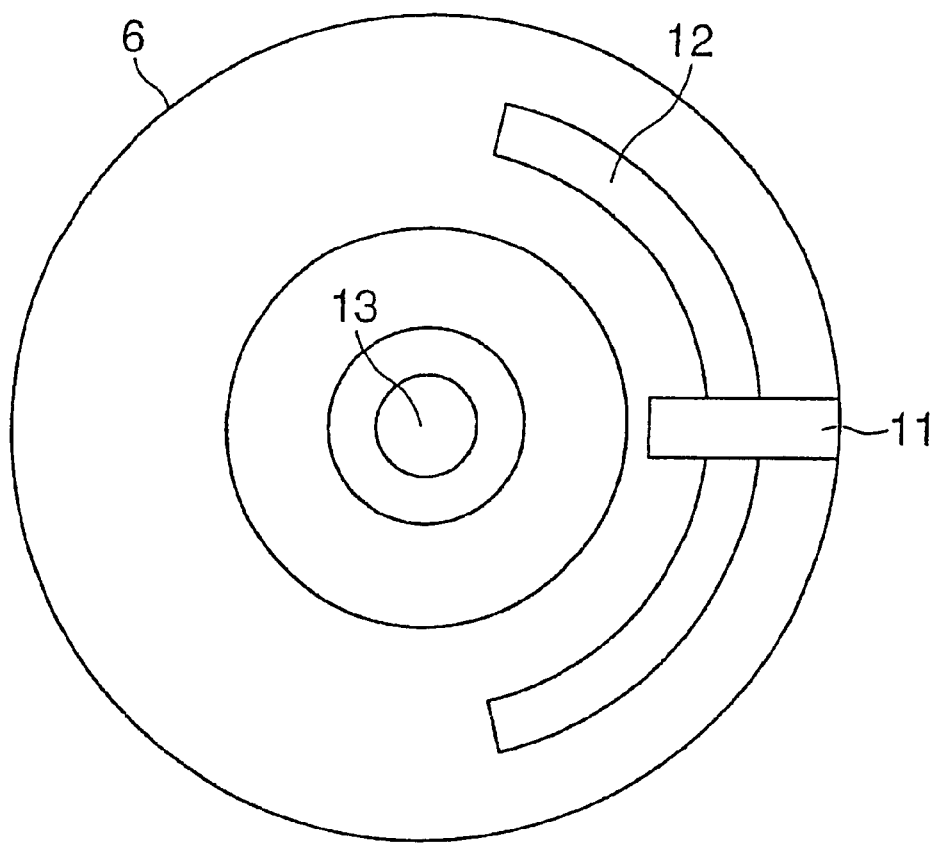
FIG. 14 is a rear plant view of a conventional mounting disk.
Figure 15:
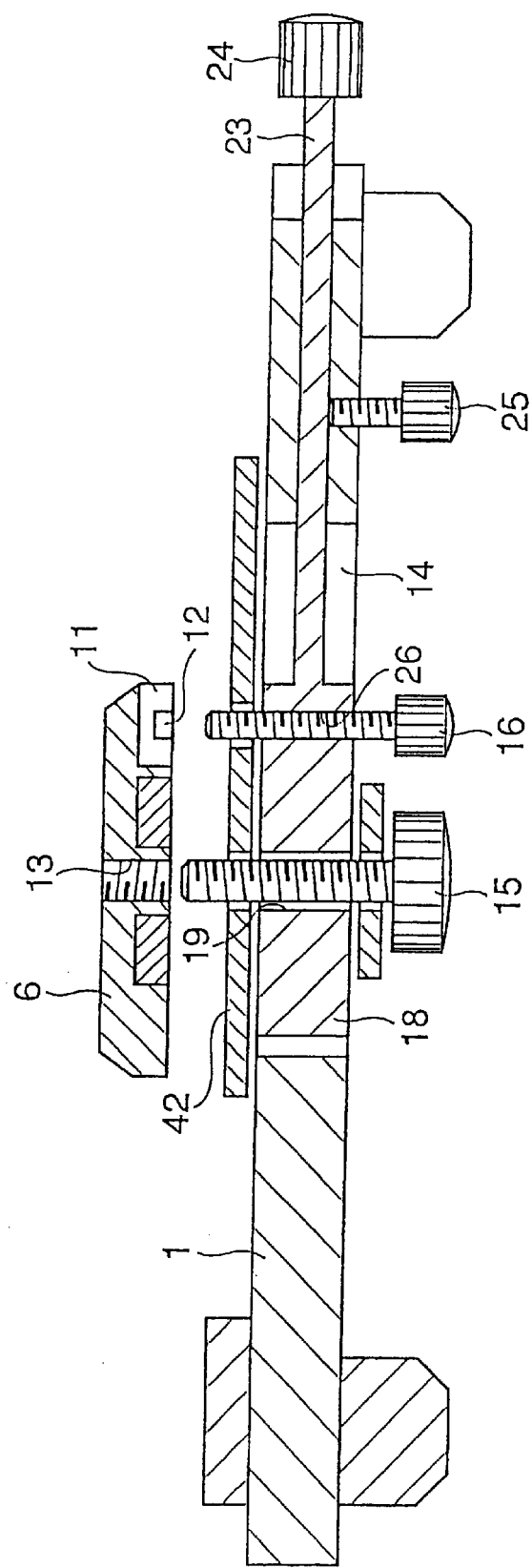
FIG. 15 is a longitudinal sectional view of a conventional mounting disk.

For the offset of the incisors in the right-to-left direction as shown in FIG. 11a, the entirety of the mandible die mounting disk 60 is turned in the R1 direction around the vertical rotary shaft 15 which has a rotational axis P1 in such a manner that the upper and lower median points coincide with each other, as shown in FIG. 11b. The guide screw 16 is then deeply threaded into the guide hole 75 for fixation, and the angle of rotation at that time is read from a rotary scale 86.

Figure 10A:
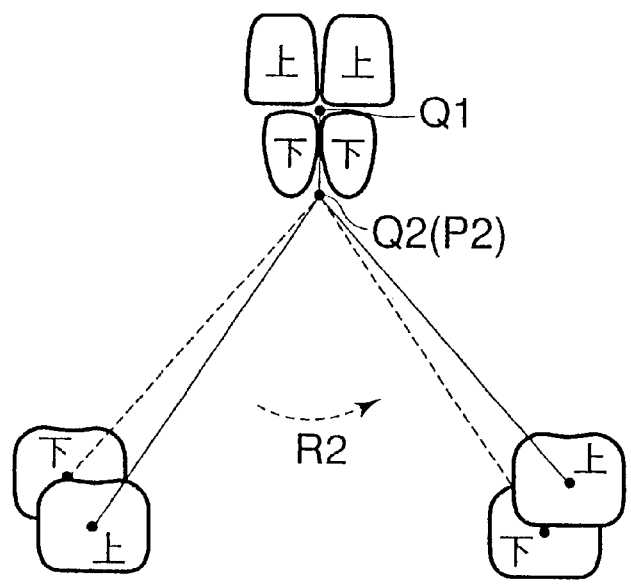
FIG. 10a is an explanatory diagram showing the method of using the mounting disk of the present invention.
Figure 10B:
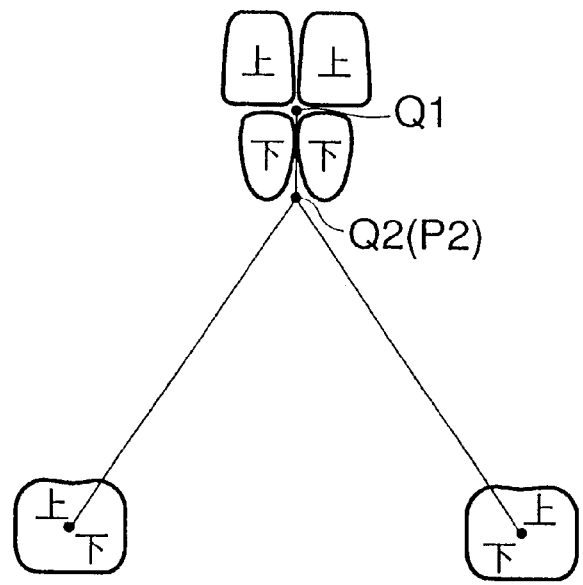
FIG. 10b is an explanatory diagram showing the method of using the mounting disk of the present invention.

In the event that the molars are offset despite the coincidence of the upper and lower median points as shown in FIG. 10a, the locking rod 81 is loosened so that the upper rotary plate 61 can turn in the R2 direction around the pivot member 64, which has a rotational axis P2 up to a position where the molars are in registration. Then the molars come into registration as shown in FIG. 10b, the locking rod 81 is tightened for fixation. The angle of rotation at that time is read from the indicator 77 and the scale 76.

The thus obtained three-dimensional orthodontia values are used to make an auxiliary tool for jaw joint positional coordination with reference to the status of the X-rayed jaw joint.

The auxiliary tool is placed between the upper and lower teeth to positionally correct the jaw joint. The auxiliary tool is usually worn while the patient is sleeping, and this auxiliary tool guides the mandible to its proper position to restore the positional relationship between the mandibular head and the joint disk to its normal position. If the mandibular head or the joint disk suffers an abrasion or damage, the auxiliary tool helps with its recover and achieves a drastic healing of a jaw joint in an abnormal condition.

In the present invention, the mandible die mounting disk for the dental articulator is divided vertically into two parts so as to permit the mandible die mounting disk to be turned around its center axis relative to the articulator base, as well as permitting it to be turned around the extremity of the mandible die mounting disk, i.e., around the median point thereof. In this way, front-to-back displacement can be measured as well as the rotational displacement relative to the dental articulator base and also the angle of offset in cases in which the molars are positionally offset irrespective of the coincidences of the median points. This makes it possible to obtain more precise fundamental data for jaw joint positional coordination.

Using the auxiliary tool for jaw joint positional coordination prepared on the basis of the fundamental data obtained using the mandible die mounting disk of the present invention, the semicircular canals are positionally modified through the rotation and displacement of the temporal bone, whereby it is possible to heal unidentified complaints such as tinnitus and dizziness.

While illustrative and presently preferred embodiments of the present invention have been described in detail herein, it is to be understood that the inventive concepts may be otherwise variously embodied and employed and that the appended claims are intended to be construed to include such variations except insofar as limited by the prior art.

What is claimed is:

1. A mounting disk comprising a lower rotary plate having at its substantially central portion a mounting portion for a vertical rotary shaft for mounting to a base of an articulator, and an upper rotary plate superimposed on top of said lower rotary plate, said upper rotary plate having on its top surface a mandible model fixing portion for mounting a mandible model thereon, said lower rotary plate and said upper rotary plate being rotatably coupled to each other by way of a pivot member disposed at one end of each of said lower an upper rotary plates;

said mounting disk further comprising indication means indicative of a relative position between said lower rotary plate and said upper rotary plate and locking means arranged to lock a relative position between said lower rotary plate and said upper rotary plate;

said locking means including an arcuate skirt, a horizontally extending slit formed in said skirt, and a locking rod passing through said slit, said arcuate skirt being formed by extending said arcuate surface of said other of said lower rotary plate and said upper rotary plate so as to cover said indication scale provided on said arcuate surface of said one of said lower rotary plate and said upper rotary plate, said locking rod having an extremity screwed into a threaded hole formed in said arcuate surface having said indication scale, said locking rod having at its midway an enlarged portion to fixedly tighten said skirt.

* * * * *